United States Patent
Stone et al.

(10) Patent No.: US 9,662,107 B2
(45) Date of Patent: May 30, 2017

(54) METHODS AND APPARATUSES FOR SECURING SUTURE

(71) Applicant: Biomet Sports Medicine, LLC, Warsaw, IN (US)

(72) Inventors: Kevin T. Stone, Winona Lake, IN (US); Troy M. Walters, Plymouth, IN (US); Gregory J. Denham, Warsaw, IN (US); Nathanael K. Conner, Huntertown, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 672 days.

(21) Appl. No.: 13/964,547

(22) Filed: Aug. 12, 2013

(65) Prior Publication Data
US 2013/0331885 A1  Dec. 12, 2013

Related U.S. Application Data (60) Division of application No. 12/941,592, filed on Nov. 8, 2010, now Pat. No. 8,506,596, which is a continuation of application No. 11/386,068, filed on Mar. 21, 2006, now Pat. No. 7,828,820.

(51) Int. Cl.
*A61B 17/04* (2006.01)
*A61B 17/064* (2006.01)
*A61B 17/00* (2006.01)

(52) U.S. Cl.
CPC ...... *A61B 17/0642* (2013.01); *A61B 17/0401* (2013.01); *A61B 2017/00477* (2013.01); *A61B 2017/044* (2013.01); *A61B 2017/045* (2013.01); *A61B 2017/0445* (2013.01); *A61B 2017/0458* (2013.01); *A61B 2017/0459* (2013.01); *A61B 2017/0477* (2013.01)

(58) Field of Classification Search
CPC ............ A61B 17/0401; A61B 17/0642; A61B 2017/00477; A61B 2017/0445; A61B 2017/0458; A61B 2017/0477; A61B 2017/044; A61B 2017/0459
See application file for complete search history.

(56) References Cited

U.S. PATENT DOCUMENTS

| | | | |
|---|---|---|---|
| 4,870,957 A | 10/1989 | Goble et al. | |
| 5,456,685 A | 10/1995 | Huebner | |
| 5,486,197 A | 1/1996 | Le et al. | |
| 5,522,843 A | 6/1996 | Zang | |
| 5,545,180 A | 8/1996 | Le et al. | |
| 5,571,139 A | 11/1996 | Jenkins, Jr. | |
| 5,584,835 A | 12/1996 | Greenfield | |
| 5,690,676 A * | 11/1997 | DiPoto | A61B 17/0401 606/232 |
| 5,702,397 A | 12/1997 | Goble et al. | |

(Continued)

*Primary Examiner* — Todd J Scherbel
*Assistant Examiner* — Son Dang
(74) *Attorney, Agent, or Firm* — Schwegman Lundberg & Woessner, P.A.

(57) ABSTRACT

Various suture anchors and surgical methods are provided. A two-part suture anchor is provided having a continuously threaded anchor body defining an axial bore and a pin. The pin includes a tip and a plate defining at least two suture receiving openings aligned in a single plane that is perpendicular to the longitudinal axis of the axial bore is disposed in anchor body. Methods of attaching soft tissue to bone are also provided.

21 Claims, 11 Drawing Sheets

(56) References Cited

U.S. PATENT DOCUMENTS

| | | | |
|---|---|---|---|
| 5,733,307 A * | 3/1998 | Dinsdale | A61B 17/0401 606/104 |
| 5,860,978 A | 1/1999 | McDevitt et al. | |
| 5,868,789 A | 2/1999 | Huebner | |
| 5,957,924 A | 9/1999 | Tormala et al. | |
| 6,517,542 B1 | 2/2003 | Papay et al. | |
| 6,666,877 B2 | 12/2003 | Morgan et al. | |
| 6,840,953 B2 | 1/2005 | Martinek | |
| 7,137,996 B2 | 11/2006 | Steiner et al. | |
| 7,144,413 B2 | 12/2006 | Wilford et al. | |
| 7,517,357 B2 | 4/2009 | Abrams et al. | |
| 7,588,587 B2 | 9/2009 | Barbieri et al. | |
| 7,828,820 B2 | 11/2010 | Stone et al. | |
| 8,133,258 B2 | 3/2012 | Foerster et al. | |
| 8,506,596 B2 | 8/2013 | Stone et al. | |
| 2002/0147463 A1 | 10/2002 | Martinek | |
| 2002/0156476 A1 | 10/2002 | Wilford | |
| 2003/0023268 A1 | 1/2003 | Lizardi | |
| 2003/0125749 A1 | 7/2003 | Yuan et al. | |
| 2004/0002735 A1* | 1/2004 | Lizardi | A61B 17/0401 606/232 |
| 2004/0147929 A1 | 7/2004 | Biedermann et al. | |
| 2005/0203620 A1* | 9/2005 | Steiner | A61L 27/386 623/13.14 |
| 2006/0079904 A1 | 4/2006 | Thal | |
| 2006/0235413 A1 | 10/2006 | Denham et al. | |
| 2006/0276841 A1 | 12/2006 | Barbieri et al. | |
| 2007/0203498 A1 | 8/2007 | Gerber et al. | |
| 2008/0275469 A1 | 11/2008 | Fanton et al. | |
| 2011/0005426 A1 | 1/2011 | Tanaka et al. | |

\* cited by examiner

METHODS AND APPARATUSES FOR SECURING SUTURE

CROSS-REFERENCE TO RELATED APPLICATIONS

This application is a divisional of U.S. patent application Ser. No. 12/941,592, filed on Nov. 8, 2010, which is a continuation of U.S. patent application Ser. No. 11/386,068 filed on Mar. 21, 2006, now U.S. Pat. No. 7,828,820 issued on Nov. 9, 2010. The entire disclosures of the above applications are incorporated herein by reference.

FIELD

The present teachings relate to methods and apparatuses for securing suture. In particular, the present teachings relate to suture anchors for securing a soft tissue to bone.

BACKGROUND

Surgical or medical procedures are often performed on a body, for example a human body or anatomy, to repair or replace various portions thereof. For example, the soft tissues of the body may need to be reattached to bones due to trauma, overuse, surgical intervention, or disease.

Soft tissue can be reattached to bone using devices such as screws, staples, and various types of suture anchors. Soft tissues are often fixed to various positions on the bone. For example, to replace a natural tendon fixation point or to replace the tendon itself, fixing a graft to a selected bone area may be desired. One means to fix the soft tissue to the selected area is to provide a suture through a selected portion of the soft tissue and fix the other end of the suture to a selected area on the bone. Various structures can be provided to anchor or hold the suture in the selected bone area.

Although suture anchors do provide a member to fix the suture to a selected portion of a boney portion, it is often desired to provide a suture anchor that will place the suture in close proximity with the tissue, particularly in articulating surfaces. Still other suture anchors require that an opening be predrilled in the bone, when, under certain circumstances it may be desirable to leave the underlying bone intact. Still other situations require that more than one suture be delivered to the implant site without significant problems of overlapping suture regions and a mis-fit of the sutures within the suture anchor.

Accordingly, there is a need for a variety of improved suture anchors for use in reattaching soft tissue to bone. There is a need for surgical methods of securing soft tissue in close proximity to an articular surface. Suture anchors and surgical methods are also needed which do not require a pre-drilled hole in the bone and leave the underlying bone intact. A still further need is a suture anchor that allows for several sutures to be delivered to a surgical site and that the sutures properly fit within the suture anchor.

SUMMARY

The present teachings provide a suture anchor including a continuously threaded anchor body defining a longitudinal bore extending from an anchor proximal end to an anchor distal end and a pin having a tip at a pin distal end and a plate at a pin proximal end. The plate is adapted to fit the anchor body bore and the plate defines at least two suture receiving openings aligned in a single plane. The plane is perpendicular to the longitudinal axis of the bore.

The plate can be rectangle-shaped and define at least two suture receiving openings. The plate can be an assembly of the three attached arms to form a y-shape where each arm defines at least one suture receiving opening. The plate can include a plurality of separate arms where each arm defines at least one suture receiving opening. The plate tip can be continuously threaded. A suture can pass through the suture receiving opening to define a closed loop structure.

The bore of the anchor body can have a cross section which matches the cross section of the pin. Upon insertion of the pin into the anchor body, the load can be placed on a bore shoulder. In the alternate, the pin can have a maximum diameter that is less than the diameter of the anchor body bore. The small pin diameter provides a load alleviation mechanism where the pin can be pulled out through the anchor body when exposed to a load equal to a pull out strength of the suture. The anchor body proximal end can also include a driver receiving region.

The present teachings provide a suture anchor comprising a continuously threaded anchor body defining an axial bore extending from an anchor proximal end to an anchor distal end, where the anchor body defines an interior shoulder. The pin has a tip at a distal end and a plate at a proximal end. The plate defines at least one suture receiving opening. The plate fits into the anchor body axial bore and is supported within the anchor body by the interior shoulder. The plate can define a plurality of suture receiving openings. The tip can have a smaller diameter than the opening of the anchor body.

The present teachings provide method of preparing a suture anchor to attach a soft tissue to bone. At least one suture is loaded into at least two suture receiving openings in a pin, where the at least two suture receiving openings are aligned in a single plane. The pin is disposed in an axial bore of a continuously threaded anchor body such that the suture receiving openings are substantially perpendicular to the longitudinal axis of an axial bore in the anchor body.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses. Although certain examples and surgical methods disclosed herein may be in conjunction with labral repairs, it is understood that the suture anchors and surgical methods disclosed herein are suitable for use to affix any soft tissue to a hard tissue, such as boney tissue.

In various embodiments of the present teachings, a two-part or plate-type suture anchor 10 is provided, as depicted in FIGS. 1A through 9C. The two-part suture anchor 10 generally includes an anchor body 12 and a pin 14. Defined along the anchor body 12 is a bone engaging structure or portion, such as the helical thread 16. The thread 16 is able to engage the bone to hold the two-part anchor 10 in a selected position. The anchor body 12 defines a longitudinal bore 18. The bore 18 extends from a proximal end of the anchor body 12 to the distal end of the anchor body 12. A driver receiving region 20 is located at the proximal end of the anchor body 12. A pin receptacle 13 is located at the distal end of the anchor body to receive the pin 14. The pin 14 includes a conical tip 22 and a plate member 24. The tip 22 may be formed to substantially ease entry of the anchor 10 into the boney portion or may be formed to allow the anchor 10 to be substantially self-drilling or self-tapping. Therefore, the tip 22 can be formed to be substantially sharp or to be any other appropriate design to allow for ease of entry of the anchor 10 into the selected boney portion. The tip 22 can also include a continuation of the thread 16.

The anchor 10 can be formed of any appropriate material. The anchor 10 can be formed of a polymer or a co-polymer, such as a co-polymer of polylactic acid and polyglycolic acid LACTOSORB as sold by Biomet, Inc. of Warsaw, Ind. Any other appropriate bioabsorbable material can also be used to form the anchor 10. Also the anchor can be formed of any appropriate biocompatible material. For example, the suture anchor 10 can be formed of a metal, such as titanium, stainless steel, or alloys of cobalt, chromium, etc. The anchor 10, can also be formed of a composite material made of any of the above materials. Regardless of the selected materials, the anchor 10 is formed such that it will have a selected pull-out strength to substantially hold the suture anchor 10 in position after the suture anchor has been implanted into the bone. Generally, the anchor body 12 and the pin 14 are formed of the same material.

The threads 16 can be designed in any appropriate fashion. For example, the threads 16 can include angled surfaces which are parallel to each other. The threads 16 can be provided in a helical pattern on the anchor body 12. The threads 16 generally begin at the distal end of the anchor body 12 and are provided in a continuous pitch to the proximal end of the anchor body 12.

The anchor body bore 18 is generally of a sufficient diameter through which to allow passage of multiple pieces of suture 26 and to receive at least a region of the pin 14. The anchor body bore 18 can have a constant inner diameter. In various embodiments, the anchor body can define a shoulder 28 or other receptacle at the distal end having a cross section to mate with a region of the pin 14 within the bore 18, as described later herein. The shoulder 28 can be an internally molded region or area. The shoulder 28 is load bearing and any loads from the suture 26 or the pin 14 are transferred to the shoulder, such that the suture will not fail. The design of the shoulder 28 should be such that it does not interfere with the passage of a suture 26 through the bore 18 and to a suturing site in the body.

Figure 4A:
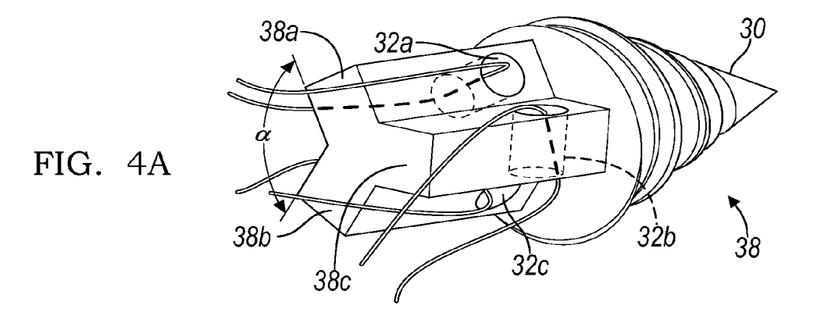
FIGS. 4A and 4B depict a Y-shaped insertion plate according to the present teachings.

The pin 14 includes a tip 22 and a plate 24. The tip 22 can be a sharp tip or can be self-tapping, or self-drilling. As depicted in FIG. 4, for example, the tip 22 can include threads 30 which span from the distal most tip (or sharp point) of the tip 22 to the proximal end of the tip 22 adjacent to the plate 24. The threads 30 can have matching pattern to the anchor body threads 16. The threads 30 can be on the tip of any of the various plate type embodiments disclosed herein.

The plate 24 includes at least two suture receiving openings 32a and 32b. Suture receiving openings as used herein refers to an at least partially voided area on the plate body to receive a suture. Exemplary suture receiving openings include slots, slits, notches, hooks, and the like and can be of any shape adapted to receive a suture. In various embodiments, the suture receiving openings are sized such that if a knot is present in the suture, the knot can freely slide through and around the opening.

Figure 1A:
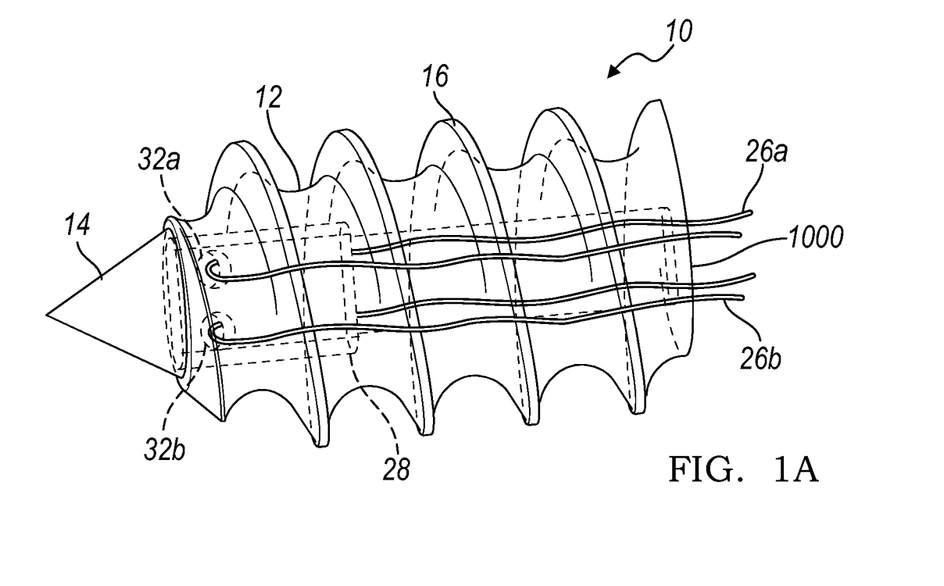
FIGS. 1A and 1B depict plate type two-part suture anchors according to the present teachings.

As shown in FIG. 1A, the plate 24 includes two suture receiving openings 32a and 32b. In embodiments having at least two suture receiving openings, the suture receiving openings 32a and 32b can be separated by any angle as long as the suture receiving openings 32a and 32b are aligned in a single plane that is perpendicular to the longitudinal axis of the bore 18. The two suture receiving openings 32a and 32b are parallel to one another. The suture 26 passes through the suture receiving openings 32a and 32b across the face of the plate 24 and through the bore of the anchor body 12. The suture 26 can also be attached to suture loops 34a and 34b located in the suture receiving openings 32a and 32b. As shown, a separate suture 26 passes through each of the suture receiving openings 32a and 32b. A single suture can be looped through both of the suture receiving openings 32a and 32b.

Figure 4B:
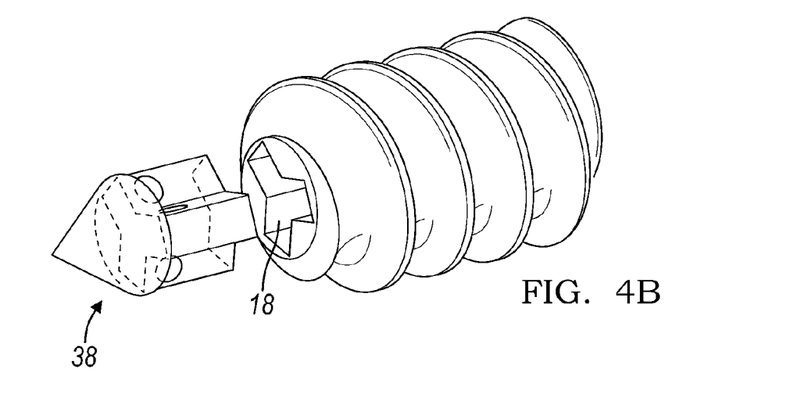

Referring to FIGS. 4A and 4B, a y-shaped plate 38 according to various embodiments is shown. The y-shaped plate 38 includes three arms 38a, 38b, and 38c each arm defining a suture receiving opening 32a, 32b, and 32c, respectively thereon. The arms 38a, 38b, and 38c are separated by angle α which is 120° and the suture receiving openings thereon are also separated by 120°. Each of the three suture receiving openings 32a, 32b, and 32c are aligned in a single plane that is perpendicular to the longitudinal axis of the bore 18 and the openings 32a, 32b, and 32c. As shown in FIG. 4B, the Y-shaped plate 38 embodiment can fit into the bore 18 with or without a matching cross section or a matching shoulder 28 so long as the bore 18 has a diameter equal to the greatest cross section of the Y-shaped plate 38. In the y-shaped plate 38 embodiment and the staggered plate 40 embodiment as shown below, it is understood that at least one of the arms or several of the arms can be used in matching the anchor body 12 cross section or mating with the shoulder 28. For example, in the y-shaped plate 38 embodiment, two of the arms can mate with the shoulder 28 instead of all three arms mating with the shoulder 28.

Figure 5:
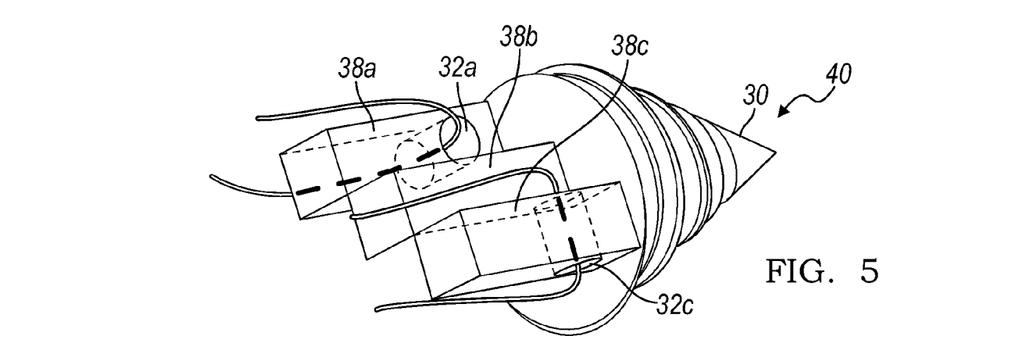
FIG. 5 depicts a multiple arm insertion plate according to the present teachings.

A staggered plate 40 is shown in FIG. 5. The staggered plate 40 includes arms 38a, 38b, and 38c which are staggered along an undersurface of the tip 22. The openings 32a, 32b, and 32c in the arms are perpendicular to the longitudinal axis of the anchor body 12. The openings 32a, 32b, and 32c are also within the same plane. The staggered plate 40 embodiment can fit into the bore 18 with or without a matching cross section or a matching shoulder 28 so long as the bore 18 has a diameter equal to the greatest cross section of the staggered plate 40. It is understood that any of the y-shaped plate 38 or staggered plate 40 can include more than one suture receiving opening per arm of the respective embodiment.

Figure 6:
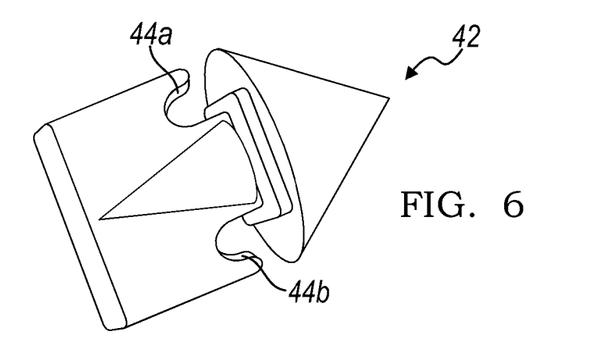
FIG. 6 depicts a plate type two-part suture anchor having J-slot suture passages according to the present teachings.
Figure 7:
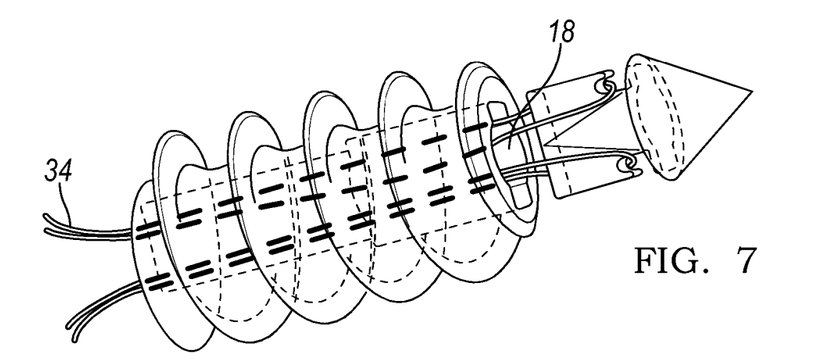
FIG. 7 depicts two sutures engaged in a partially assembled two-part suture anchor having J-slot suture passages according to the present teachings.
Figure 8:
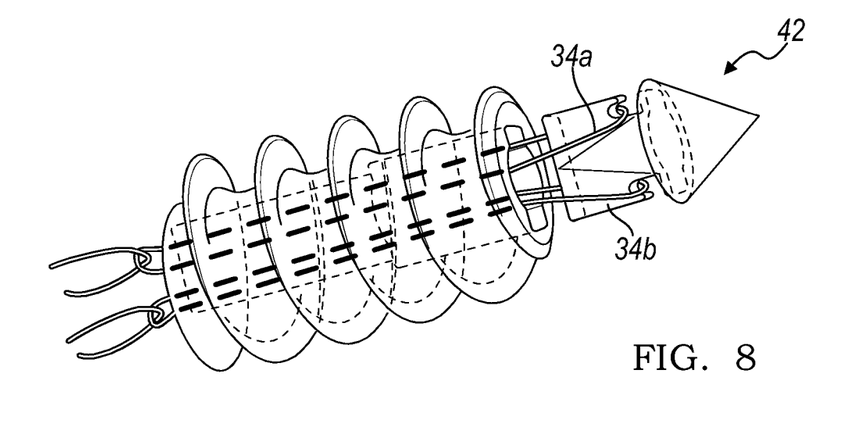
FIG. 8 depicts two suture loops secured about the J-slot suture passages according to the present teachings.

A J-slot plate 42 is shown in FIGS. 6, 7, and 8. The J-slot plate 42 includes hooks or J-slots 44a and 44b shaped like a "J" on the plate body. The J-slots 44a and 44b are not fully enclosed openings such as those in the y-shaped or staggered plate embodiments. The slots are partially open allowing the suture to be easily placed about the J-slots 44a and 44b instead of having the suture 34 looped through the opening 32a, for example. The J-slot plate 42 embodiment can fit into the bore 18 with or without a matching cross section or a matching shoulder 28 so long as the bore 18 has a diameter equal to the greatest cross section of the J-slot plate 42.

Figure 1B:
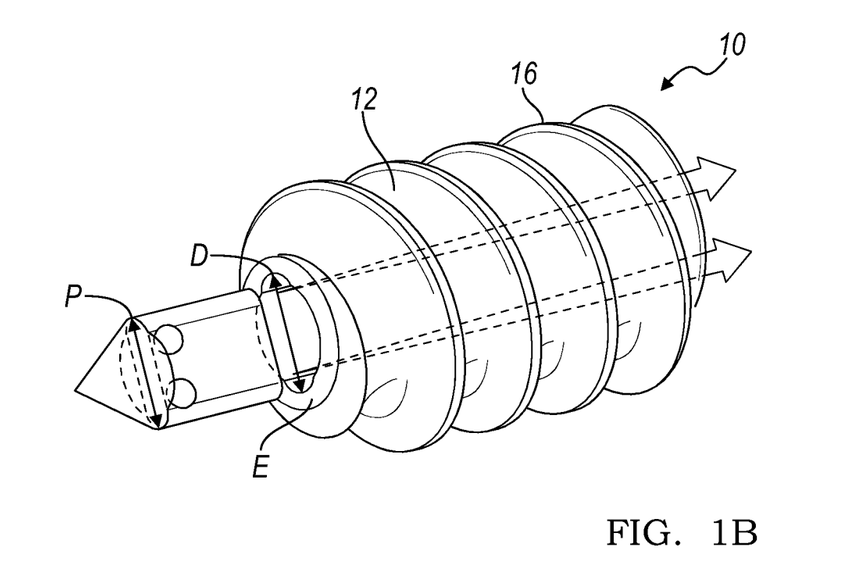
Figure 2:
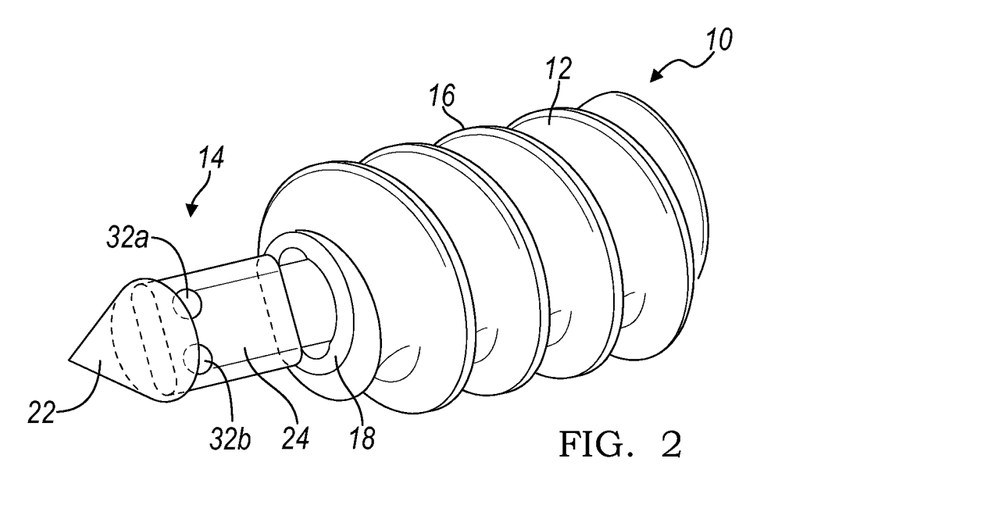
FIG. 2 depicts the components of a plate type two-part suture anchor according to the present teachings.
Figure 3:
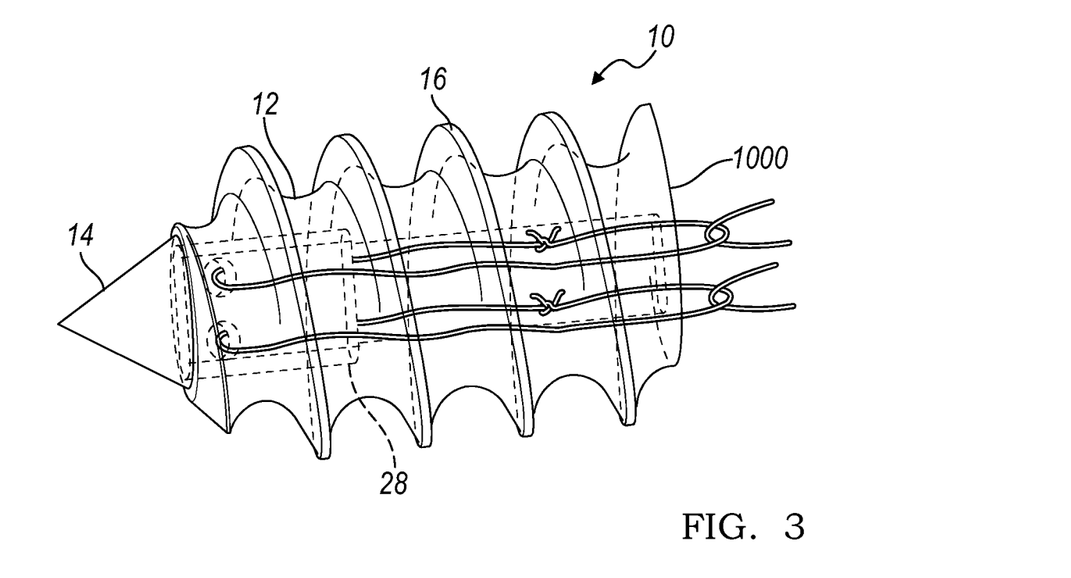
FIG. 3 depicts a plate type two-part suture anchor using a suture loop according to the present teachings.

Referring to FIG. 1B, in embodiments where the anchor body includes a load alleviation mechanism, the bore 18 has a smallest diameter D equal to or slightly greater than the greatest cross section P of the pin 14 tip 22 or the plate 24 of the pin 14. Where the bore is of a constant size, the diameter D is the diameter of the bore 18. When the bore 18 is not of a constant size, the diameter D is the smallest diameter within the bore 18. Because the cross section P is smaller than the smallest diameter D of the bore 18, the plate 24 and the tip 22 of the pin 14 can slide completely through the bore 18. The purpose of the load alleviation mechanism is to prevent breakage or failure of the suture by allowing the pin 14 holding the suture to move in the direction of the pulling force without being becoming lodged in the bore 18. For example, when a load is placed on the suture that is sufficient to cause suture failure, the pin 14 is withdrawn from the bore 18 in the direction of the force to prevent the entire load from being placed on the suture.

Figure 9A:
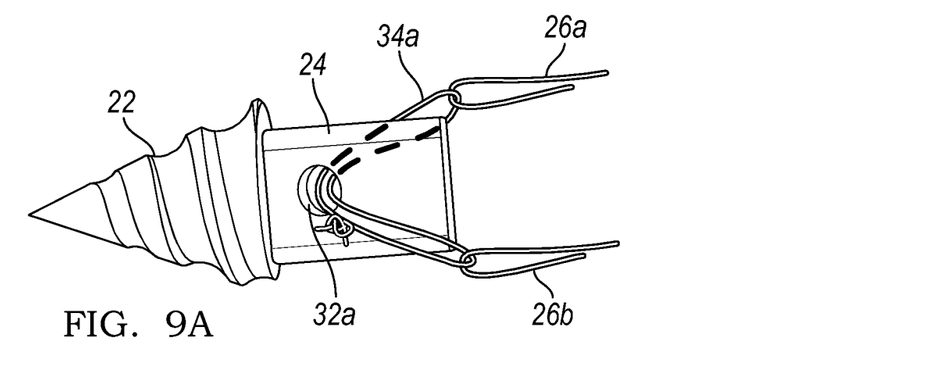
FIGS. 9A, 9B, and 9C depict a single opening plate type suture anchor.
Figure 9B:
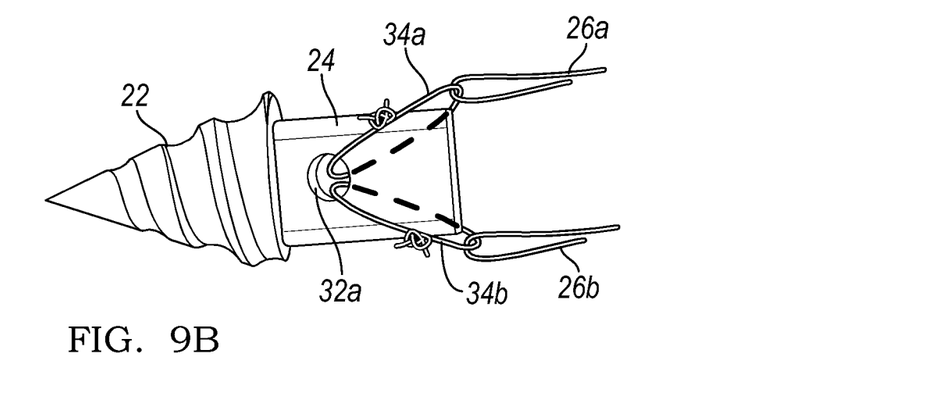
Figure 9C:
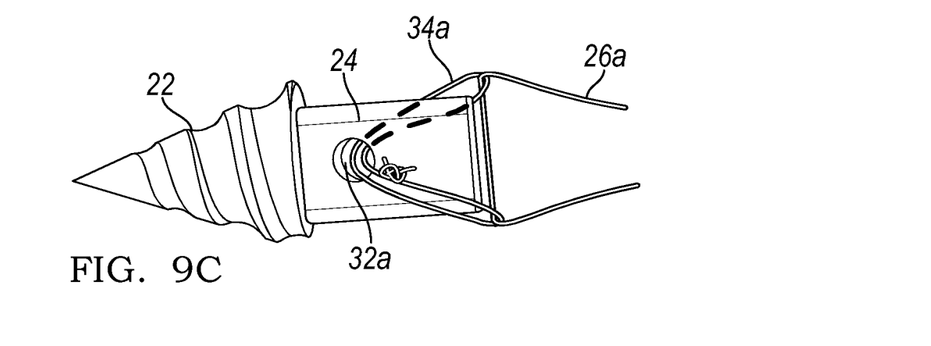

Referring to FIGS. 9A, 9B, and 9C, a plate type suture anchor as described above with slight modifications is provided. The plate 24 includes a single opening 32a for a suture. The plate 24 is supported by the shoulder 28 on the interior of the anchor body. In such embodiments, the tip 22 can be a smaller diameter than the distal opening of the anchor body 12. By removing load from the edge E or outer perimeter of the anchor body 12 distal end advantageously places the load from the sutures on the shoulder 28.

Sutures 26 can be provided in a variety of ways using the single plate embodiment, or any of the other plate type embodiments. As shown in FIG. 9A, a suture 26 is knotted to form a loop 34a. The loop 34a is folded through the suture receiving opening 32a such that the two ends of the suture loop are available to dispose two or more pieces of free suture 26a and 26b. As shown in FIG. 9B, two suture loops 34a and 34b are disposed in the suture receiving opening 32a and each loop 34a and 34b has a suture 26a, 26b disposed therein. As shown in FIG. 9C, the loop 34a is folded through the suture receiving opening 32a similar to the folding shown in FIG. 9A. The ends of the suture loop 34a are joined with a single piece of suture 26a. Any combination of suture loops 34a or sutures can be used with any of the plate embodiments disclosed herein.

A method for preparing the anchor for use is provided. While the method is described in connection with the rectangle-shaped plate, the preparation technique can similarly be used with any of the plate embodiments disclosed herein. To prepare the anchor 10 for use, sutures 26 or the suture loops 34a and 34b are thread, or laced, or looped through the openings 32a and 32b in the plate 24. The threading, lacing, or looping can include any of the threading or looping styles disclosed in conjunction with FIGS. 1A through 9C regardless of the number of suture openings or sutures employed. The plate 24 is then aligned with the anchor body bore 18 such that upon advancing the plate 24 proximally, the plate 24 and the sutures 26 or suture loops 34a and 34b contained thereon are in the anchor body and the tip 22 extends from the distal end of the anchor body.

To engage the anchor 10 for placement within a tissue, a driver engaging region 1000 is located at the distal end of the anchor body 12. The driver region 1000 is adapted to receive a tool or driver 1010, such as those in FIGS. 20A, 20B, 21A, 21B, 22 and 23. The driver engaging region 1000 can include a substantially hexagonal perimeter to be received within a substantially hexagonal socket or drive tool. As a further example, various recesses can be formed substantially on the end of the driver engaging region 1000 to be operated by a screw driver having a complimentary blade for example, to drive the suture 10 into the selected boney portion. The driver 1010 can include various combinations to mate the end of the anchor with the driver 1010, such as the male 1020 and female 1030 and the driver 1010 can include a suture receiving area 1040 as shown in FIGS. 20A, 20B, 21A, 21B, 22 and 23.

With reference to FIGS. 10 through 14, a asymmetric suture anchor 100 according to a various embodiments of the present teachings is provided. The asymmetric suture anchor 100 includes a tip 102, an anchor body 104 having an interior bore 106, an exterior suture receiving channel 108 defined by one side of the anchor body, and a port 110 connecting the interior bore 106 and the exterior suture receiving channel 108. The anchor can be made of any of the materials disclosed earlier herein in connection with the plate-type suture anchor 10.

At the distal end of anchor 100, the tip 102 is adapted to substantially ease entry of the asymmetric anchor 100 into the bone portion. The tip 102 may be generally smooth or rounded such that the anchor 100 can be pushed or screwed into a pre-drilled hole in a boney tissue to reattach a soft tissue thereto without damaging the soft tissue.

Attached to the tip 102 is the anchor body 104. The anchor body 104 can be externally threaded or have helical or annular ribs. The threading 16 can be a helical thread which starts at the meeting point of the tip 102 and the anchor body 104. The threads 111 facilitate engagement of the tissue by the asymmetric anchor 100.

A bore 106 in the anchor body 104 extends from a proximal end of the anchor body 104 through an interior portion of the anchor body. The bore generally extends along the longitudinal axis of the anchor body 104 and is open at the proximal end. The bore 106 can be offset with the outer diameter of the anchor body or the bore 106 can be concentric with outer diameter of the anchor body. The bore 106 provides an area in which a region of suture can be placed in the interior of the anchor body 104. The bore 106 is sufficiently sized to allow for the passage of a suture knot therethrough as discussed later herein.

The bore 106 is connected to a suture receiving channel 108 with the port 110. The suture receiving channel 108 is located on an exterior surface of the anchor body 104. The suture receiving channel 108 provides an area in which a region of suture 26 can be placed on the exterior of the anchor body 104.

The port 110 connecting the suture receiving channel 108 and the interior bore 106 is generally perpendicular to at least one of the suture receiving channel 108 and the interior bore 106. The port 110 provides the communication between the inside of the anchor (interior bore 106) and the outside of the anchor (suture receiving channel 108). The port 110 is sized to receive a loop of suture. As shown, the port 110 and the external channel 108 partially extend into the tip 102 and provide a break in the threading 111. In embodiments where a suture loop is employed, the port is of a sufficient diameter to allow for passage of a knot. The port 110 can have the same diameter as the interior bore 106. In various embodiments, the port 110 diameter, the interior bore 106 diameter, and the cross section of the suture receiving channel 108 are the same. By providing an anchor 100 which can freely accept a knot sliding through the offset or asymmetrical opening formed in the anchor 100 provides stability to the anchor 100 because the anchor will not toggle when stress is placed on the anchor 100.

The suture receiving channel 108 and the bore 106 are considered to be offset or asymmetrical due to the suture 26 being partly received in the interior of the anchor body 104 at the bore 106 and partly received in the exterior of the anchor body 104 at the suture receiving channel 108. The combination and arrangement of the bore 106, the suture receiving channel 108, and the port 110 form a continuous track or loop around which a suture 26 can be wrapped.

Figure 10:
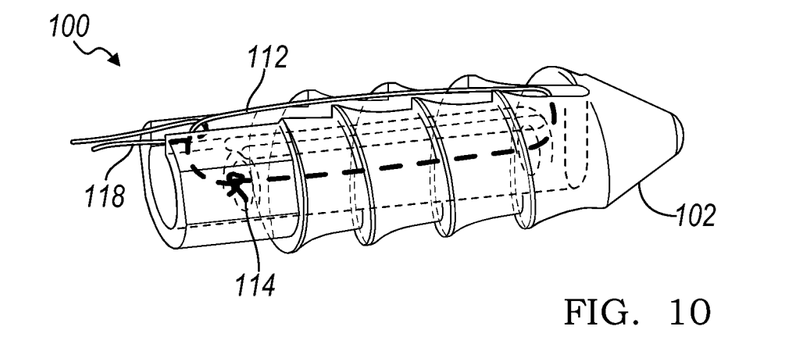
FIG. 10 depicts a suture anchor having a single external channel according to the present teachings.
Figure 11:
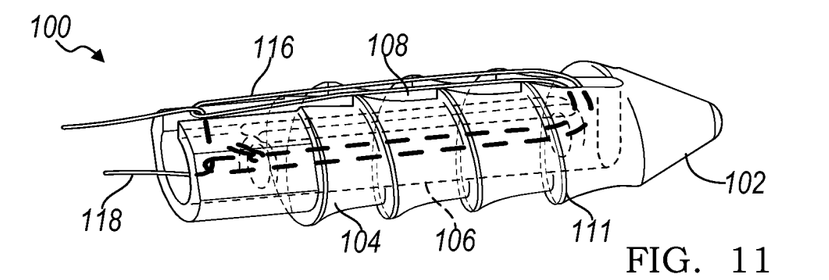
FIG. 11 depicts a double looped suture disposed within a suture anchor having an external channel according to the present teachings.
Figure 12:
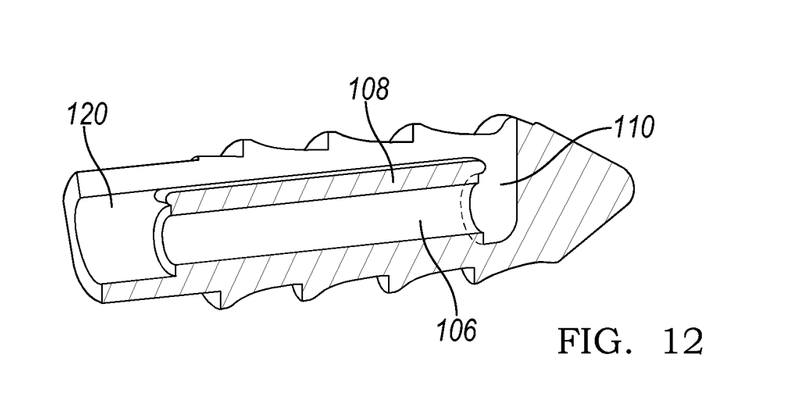
FIG. 12 depicts a cut away view of a suture anchor of FIG. 10.
Figure 13:
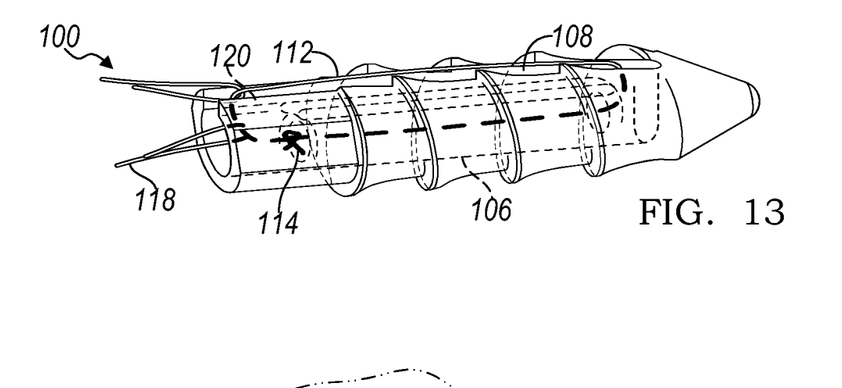
FIG. 13 depicts the passage of a suture knot within the suture anchor of FIG. 10.

As shown in FIGS. 10 and 11, in various embodiments, the suture is a loop 112 of suture having a knot 114. The knot 114 is generally small and strong. The knot 114 is sufficiently small to freely slide about the continuous track formed by the bore 106, the suture receiving channel 108 and the port 110. In other embodiments the suture 26 is a loop that is doubled back to provide a "saddle 116 or u-shaped loop structure. The saddle 116 provides an attachment site for multiple pieces of free suture (or non-looped suture) 118 used to suture the tissue. The loop either as unfolded or as doubled back to provide the saddle 116 disperses the forces placed on the free suture 118 which is folded over the loop 112 or saddle 116, as depicted. The flexing of the suture loop 112 or saddle 116 and the flexing of the free suture 118 provides better strength to the sutures as loads from movement of the free suture 118 or the suture loop 112 or saddle 116 are not against the rigid and inflexible structure of the anchor body, but instead the loads from movement are flexed and dispersed between the suture loop 112 or saddle 116 and the free suture 118. The loop 112 or saddle 116 extends out of the anchor body 104 to allow for attachment of the free suture. As shown in FIG. 12, multiple free sutures are attached to the suture loop 112.

The asymmetric suture can include a proximal end groove 120 to receive the suture and accommodate the free sliding of the suture loop. The proximal end groove 120 is in communication with the opening at the proximal end of the anchor body 104.

Figure 22:
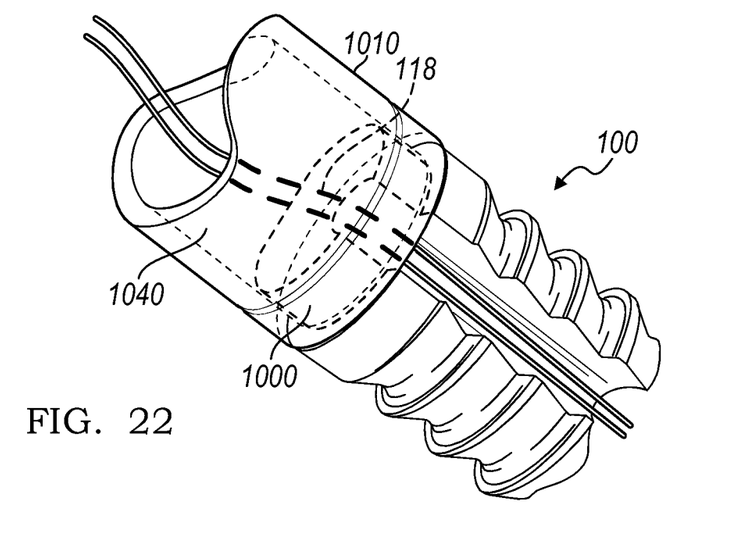
FIG. 22 depicts a rear isometric view of a driver according to the present teachings.
Figure 23:
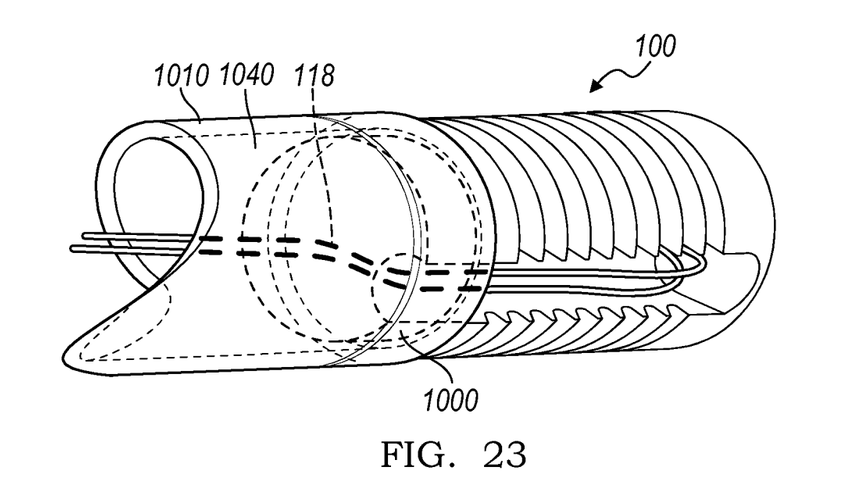
FIG. 23 depicts a rear side view of a driver and a suture anchor according to the present teachings.

The proximal end of the suture anchor 100 also includes a driver engaging region 1000, such as those detailed earlier herein. Particular to the asymmetric anchor, the proximal end groove 120 can be provided with driver engaging features 121, depicted as dimples which will go into the female driver that contains notches matching the dimple profile. As shown in FIGS. 22 and 23, the suture being carried is protected within the suture receiving area 1040.

The asymmetric anchor 100 is inserted into the tissue in an angle or position which corresponds to the desired final placement. The asymmetric anchor does not toggle and is not otherwise moved after insertion.

Figure 14:
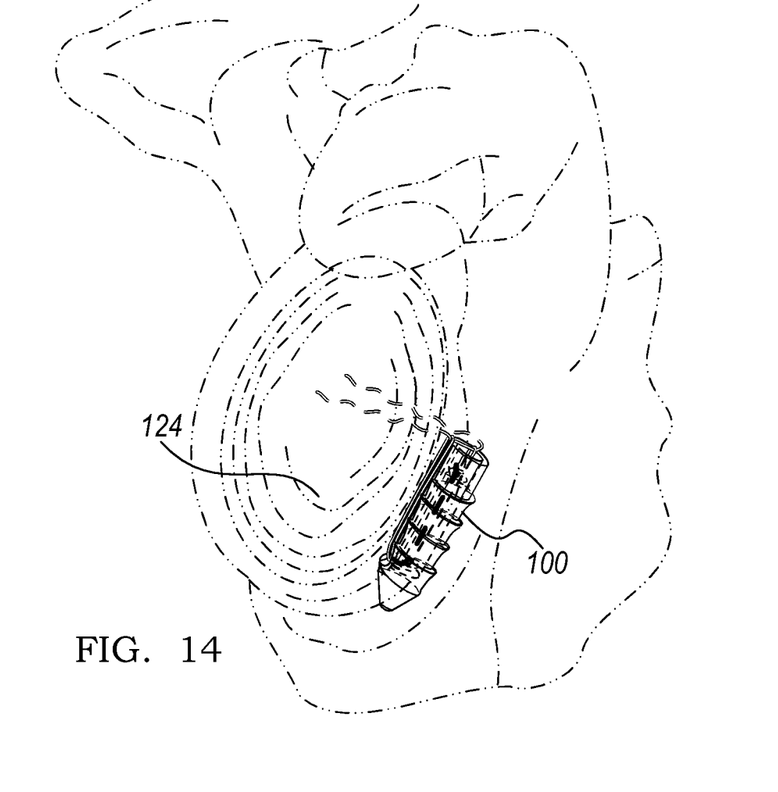
FIG. 14 depicts the single external suture channel anchor used to secure a tissue according to the present teachings.

FIG. 14 depicts placement of a asymmetric anchor 100 in a shoulder using surgical methods according to the present teachings. A continuous loop of suture 112 or a suture saddle 116 is offset in an anchor body 104 by disposing a region of the suture loop in the bore 106 and disposing a region of the suture loop in the exterior suture receiving channel 108. The anchor body 104 is fixed to an area adjacent the defect such that the suture loop 112 or the suture saddle 116 and the channel 108 abut the defect. The defect is sutured with the free suture 118 to retain the anchor body in abutment with the defect site.

Abutting the offset or the channel 108 area of the anchor body 104 against the defect site minimizes the length of suture that remains between the beginning of the available or suturable suture in the bone tunnel and the tissue to be sutured. When the offset or channel 108 area of the anchor body 104 abuts the defect site, the repair is stronger due to the ability to more tightly secure the tissue to the underlying bone and minimizing the gap or lag between the anchor body 104 and the tissue. A close proximity between the tissue and the anchor is particularly useful in repairing soft tissue defects, for example, a labral tear. The anchor body proximal end would abut the labrum 124 and provide strong attachment and promote healing of the labral tear and restore strength to the shoulder or the hip, for example.

Figure 15:
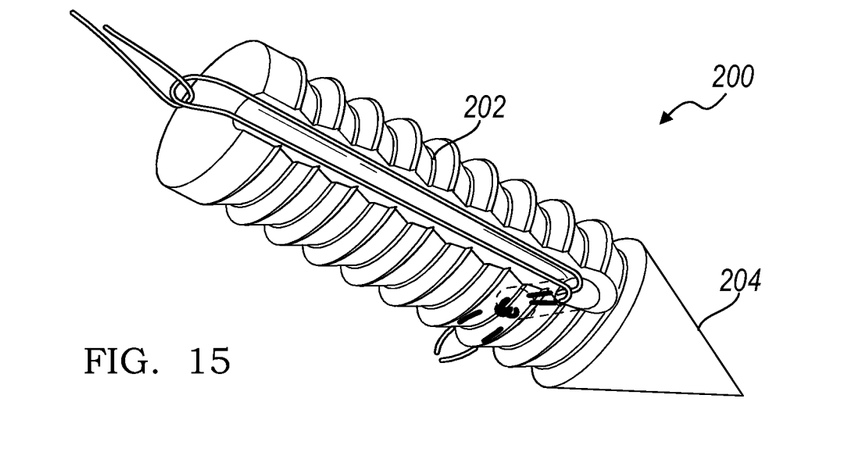
FIG. 15 depicts a direct insertion suture anchor according to the present teachings.
Figures 16A, 16B:
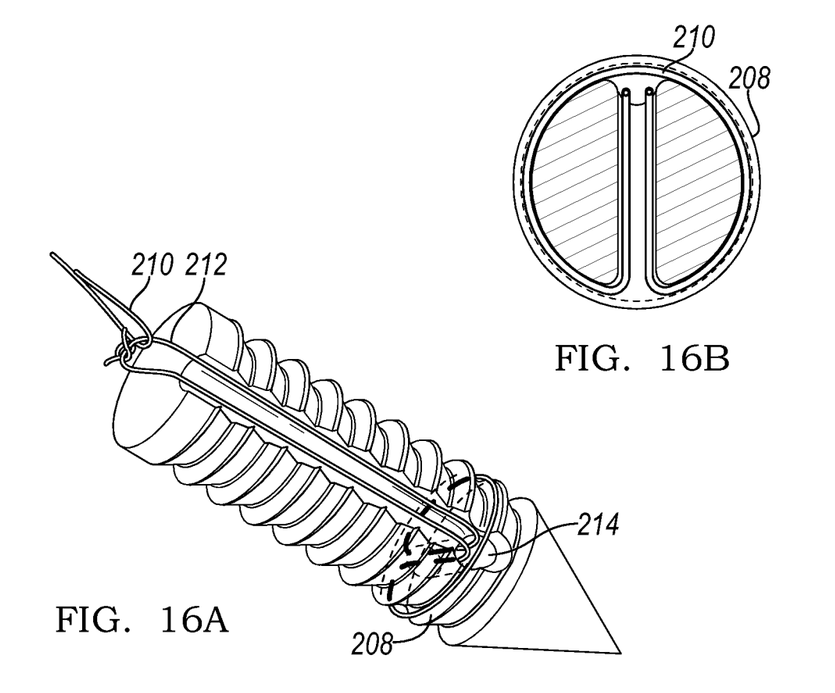
FIGS. 16A and 16B depict a direct insertion suture anchor according to the present teachings.

Referring to FIGS. 15, 16A, and 16B, a resorbable direct insertion suture anchor 200 according to various embodiments is provided. The resorbable direct insertion suture anchor 200 materials are strong enough to allow the anchor to be impacted directly into unmodified bone or bone that does not have a pre-drilled hole or opening therein.

The resorbable direct insertion suture anchor 200 includes an anchor body 202 and a tip 204 at the distal end for impacting into bone. The resorbable direct insertion suture anchor 200 is made of a composite of an osteoconductive ceramic and a resorbable polymer. The osteoconductive ceramic can include any ceramic material which contributes to bone growth. Suitable osteoconductive ceramic materials include, but are not limited to hydroxyapatite, calcium phosphate, tricalcium phosphate, and combinations thereof. Any other ceramic material which contributes to bone ingrowth can be substituted for the listed materials. The resorbable polymer can include any polymer or copolymer which is resorbed by the body. Suitable resorbable polymers include, but are not limited to polylactic acid, polyglycolic acid, and combinations thereof.

The resorbable polymer anchor body 202 can include threads 206. The threads are similar to the threads disclosed earlier herein and are generally continuous threads. The threads 206 can have a continuous pitch and the threads can be helical threads.

The anchor body 202 can include various receptacles for suture. For example, as shown in FIGS. 16A and 16B, the anchor body 202 can include a neck region 208 about which a suture 210 or a suture loop 212 may be placed. The suture 210 or the suture loop 212 can be wrapped around the neck region 208 to be carried by the anchor 200 into a soft tissue and a boney tissue. The neck region 208 as depicted is located between the anchor tip 204 and the anchor body 202. It is understood that the neck 208 can be located anywhere along the anchor body 202. The anchor 200 can also include a longitudinal channel on the exterior of the anchor body 202 to guide the suture or suture loop.

In various embodiments, the anchor body 202 includes an axial bore 214 through the neck 208 through which the suture 210 or the suture loop 212 can pass. As shown in FIG. 16B, the suture loop 212 is passed through the neck and wrapped back about the neck similar to the looping of a pretzel. The looping of the suture 210 or the suture loop 212 improves the strength at which the suture can be pulled prior to breaking. As stated above herein, the suture loop 212 can be connected to free suture 210 such that pressure on either the suture loop 212 or the free suture 210 causes the other to flex instead of pulling against the rigid anchor body 202 and potentially breaking the suture 210 or the suture loop 212.

Any of the drivers 1010 such as those disclosed earlier herein can be used with the suture anchor 200. The direct insertion suture anchor 200 can have a flat drive end such that the anchor 200 is impacted or hammered by a tool. Placement of the direct insertion suture anchor 200 is best illustrated in the following method.

A surgical method particular to the direct insertion suture anchor 200 is also provided. The suture anchor 200 is oriented with respect to a region of unmodified bone. Unmodified bone refers to bone that has not been pre-drilled or otherwise has a hole to receive a suture anchor. The suture anchor tip 204 is directed downwards towards the unmodified bone. The proximal end of the suture anchor 204 is hit with an impaction tool, such as a hammer, or any type of driver and the suture anchor 204 pierces the bone and becomes lodged in the unmodified bone. The surgical method is advantageous because it prevents the use of a pre-drilled hole in bone.

Figure 17:
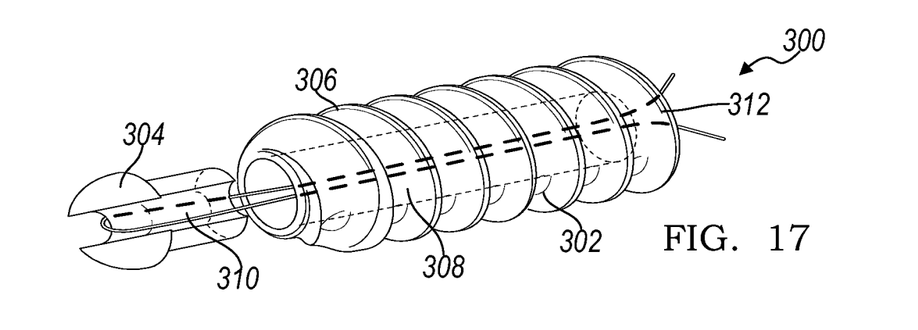
FIG. 17 depicts a threaded suture anchor having a cap at the distal end to seat a suture.

Referring to FIG. 17, an embodiment of a cap looped suture anchor 300 according to the present teachings is provided. The cap looped suture anchor 300 can be made of any of the materials disclosed earlier herein. The cap looped anchor 300 is a two part anchor including a suture anchor body 302 and a cap 304. The suture anchor body 302 has threads 306 thereon. The anchor body 302 includes a throughbore 308 to accept a suture cap 304. The suture cap 304 includes a groove 310 around which a suture is placed. The suture cap 304 is advanced proximally into the throughbore 304 to secure the suture therein. The cap looped anchor 300 includes a driver engaging feature 312 whereby the anchor 300 can be impacted into a pre-formed hole in bone or can be otherwise inserted using the drivers as disclosed above.

Figure 18:
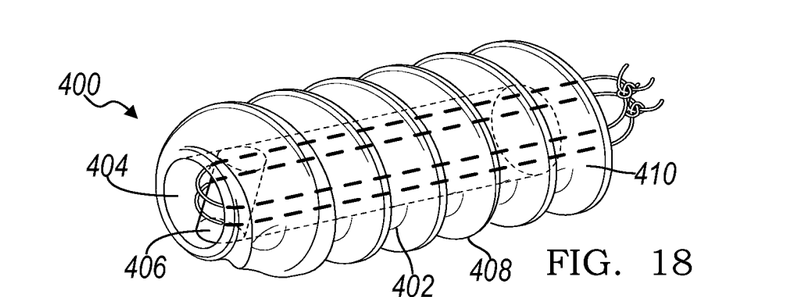
FIG. 18 depicts a one-piece threaded suture anchor having an internal molded pin.

Referring to FIG. 18, an embodiment of a suture anchor according to the present teachings is provided. The internal pin anchor 400 can be made of any of the materials disclosed earlier herein. The internal pin anchor 400 is a one-piece anchor body 402 having a pin 406 molded into the bore 404 of the anchor body 402. A suture is looped over the pin 406 and passes through a proximal end of the internal pin anchor 400. The anchor body 402 can include threading 408 such as the threading disclosed earlier herein. The internal pin anchor 400 includes a driver engaging feature 410 whereby the anchor 400 can be impacted into a pre-formed hole in bone or can be otherwise inserted using the drivers as disclosed above.

Figure 19:
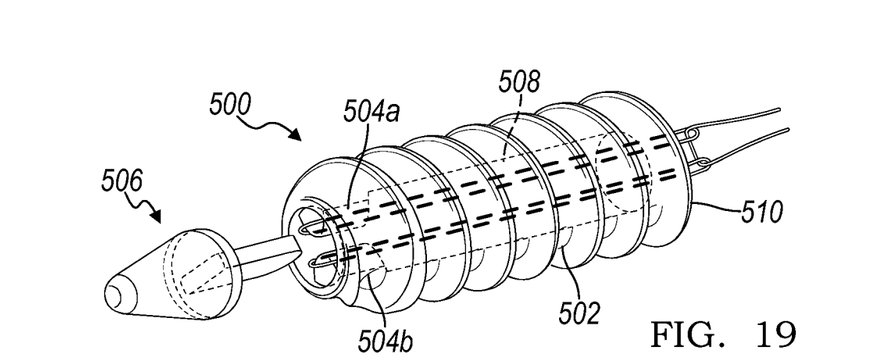
FIG. 19 depicts a two-piece threaded suture anchor having two internal bosses and a plate insertion tip.
Figure 20A:
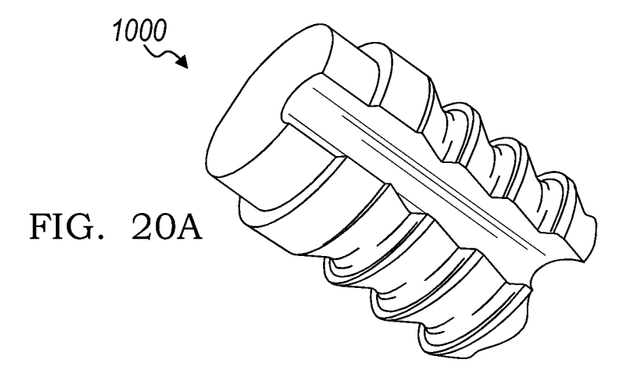
FIGS. 20A and 20B depict driver or tool receiving ends for the various suture anchors according to the present teachings.
Figure 20B:
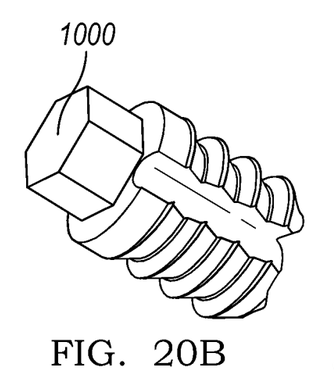
Figure 21A:
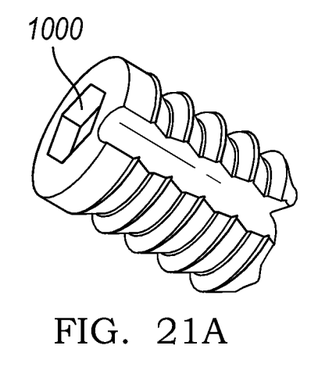
FIGS. 21A and 21B depict various driver or tool receiving ends of the suture anchors according to the present teachings.
Figure 21B:
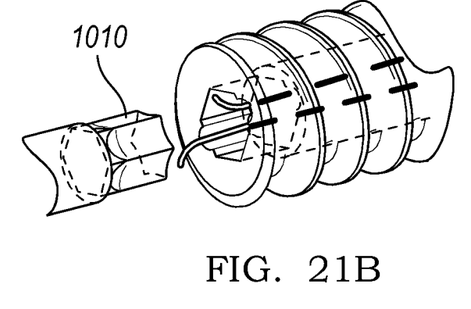

Referring to FIG. 19, an embodiment of an internal boss suture anchor 500 according to the present teachings is also provided. The internal boss suture anchor 500 can be made of any of the materials described earlier herein. The internal boss anchor 500 includes an anchor body 502 having two internal bosses 504a and 504b with a small space therebetween and a plate insertion tip 506. The anchor body includes a throughbore 508 and can have threading 510, such as the threading described above herein. In use, separate pieces of suture are looped about each of the internal bosses 504a and 504b. The plate insertion tip 506 is inserted between the internal bosses to separate the bosses 504a and 504b and provide two independent suture passages. The internal boss anchor 500 includes a driver engaging feature 510 whereby the anchor 500 can be impacted into a preformed hole in bone or can be otherwise inserted using the drivers as disclosed above.

The description of the present teachings is merely exemplary in nature and, thus, variations that do not depart from the gist of the present teachings are intended to be within the scope of the present teachings. Such variations are not to be regarded as a departure from the spirit and scope of the present teachings.

What is claimed is:

1. A suture anchor system for insertion into a portion of a patient, comprising:
    a body extending along a body axis from a proximal end to a distal end;
    a neck region formed nearer the distal end than the proximal end;
    an interior bore extending along the body axis;
    a channel formed in an exterior of the body from the neck to the proximal end;
    a transverse port extending from the channel to the interior bore; and
    a suture portion extending through the interior bore, the port, and the channel;
    wherein the body and at least the proximal end are configured to be driven directly into the portion of the patient that is unmodified.

2. The suture anchor system claim 1, wherein the distal end is formed as a conical tip.

3. The s re anchor system claim 2, wherein the plurality of radial extending protrusions are formed as a thread on an exterior of the body extending from the proximal end towards the distal end;
    wherein the conical tip is smooth.

4. The suture anchor system claim 1, further comprising: a plurality of radial extending protrusions.

5. The suture anchor system of claim 1, wherein the body is made of a composite of an osteoconductive ceramic and a resorbable polymer.

6. The suture anchor system of claim 1, wherein the port extends along a port axis through the body transverse to the body axis.

7. The suture anchor system of claim 1, wherein the channel is configured to receive an extending portion of the suture portion that extends from the port;
wherein the extending suture portion is recessed from a maximum exterior dimension of the body.

8. A suture anchor system for insertion into a portion of a patient, comprising:
a body, including:
an exterior surface extending from a tip end to a driver end;
a neck region formed near the tip end to engage a first suture portion;
an elongated channel extending from the neck region to the driver end;
a longitudinal bore extending along the interior of the body from the tip end to the driver end; and
a transverse bore extending from the longitudinal bore to the elongated channel; the first suture portion extending through the longitudinal bore, the transverse bore and the elongated channel.

9. The suture anchor system of claim 8, wherein the transverse bore is formed through the body at the neck region.

10. The suture anchor system of claim 9, wherein the first suture portion is a suture loop that extends through the longitudinal bore, the transverse bore, and the elongated channel.

11. The suture anchor system of claim 9, further comprising a thread formed by the exterior surface of the body, wherein a peak of the thread defines a maximum exterior dimension of the body.

12. The suture anchor system of claim 11, wherein the elongated channel is recessed within the maximum exterior dimension defined by the thread.

13. The suture anchor system of claim 8, further comprising a second suture portion fixed to the first suture portion;
wherein the first suture portion is fixed to the body at least by forming a loop around the body at the neck region and being passed through the longitudinal bore, the transverse bore, and the elongated channel.

14. The suture anchor system of claim 13, wherein the body is made of a composite of an osteoconductive ceramic and a resorbable polymer.

15. A method of anchoring a first suture portion with a suture anchor system in an unmodified portion of a subject, the method comprising:
fitting the first suture portion through a longitudinal bore formed in a suture anchor body that includes an exterior surface extending from a tip end to a driver end;
positioning the first suture portion through a transverse port extending from the longitudinal bore to a channel at a neck region of the suture anchor body formed adjacent to the tip end, the neck region configured to engage the first suture portion;
positioning the first suture portion in the channel that is formed in the exterior of the suture anchor body; and
driving a tip end of the suture anchor directly into the unmodified portion of the subject.

16. The method of claim 15, wherein positioning the first suture portion in the channel further comprises:
placing the second suture portion within a maximum exterior dimension of the suture anchor body.

17. The method of claim 16, wherein positioning the first suture portion at a neck region of a suture anchor body includes placing a suture loop through the suture anchor body to at least partially encircle the suture anchor body with a first portion of the suture loop.

18. The method of claim 17, wherein fitting the first suture portion through the longitudinal bore formed in the suture anchor body includes passing a second portion of the suture loop through the longitudinal bore.

19. The method of claim 18, wherein placing the first suture portion within the channel includes placing a third portion of the suture loop extending from the longitudinal bore into the channel.

20. The method of claim 16, further comprising:
positioning the tip end of the suture anchor body directly on the portion of the subject;
wherein driving the tip end of the suture anchor directly into the unmodified portion of the subject includes substantially axially driving the suture anchor body in to the unmodified portion of the subject.

21. The method of claim 20, further comprising:
connecting a soft tissue portion to the first suture portion.

* * * * *

UNITED STATES PATENT AND TRADEMARK OFFICE
CERTIFICATE OF CORRECTION

| | |
|---|---|
| PATENT NO. | : 9,662,107 B2 |
| APPLICATION NO. | : 13/964547 |
| DATED | : May 30, 2017 |
| INVENTOR(S) | : Stone et al. |

It is certified that error appears in the above-identified patent and that said Letters Patent is hereby corrected as shown below:

In the Claims

In Column 10, Line 58, in Claim 3, delete "s re" and insert --suture-- therefor

In Column 12, Line 20, in Claim 16, delete "second" and insert --first-- therefor Signed and Sealed this
Ninth Day of January, 2018

Joseph Matal
*Performing the Functions and Duties of the
Under Secretary of Commerce for Intellectual Property and
Director of the United States Patent and Trademark Office*